(12) United States Patent
Brichka et al.

(10) Patent No.: US 9,650,256 B2
(45) Date of Patent: May 16, 2017

(54) CERIUM OXIDE-ALUMINOSILICATE TUBES NANOCOMPOSITE AND METHOD OF PREPARATION

(71) Applicant: TOVARISTVO Z OBMEZHENOU VIDPOVIDALNISTU "NANOMEDTRAST", Kiev (UA)

(72) Inventors: Alla Brichka, Kiev (UA); Sergiy Brichka, Kiev (UA)

(73) Assignee: TOVARISTVO Z OBMEZHENOU VIDPOVIDALNISTU "NANOMEDTRAST", Kiev (UA)

(*) Notice: Subject to any disclaimer, the term of this patent is extended or adjusted under 35 U.S.C. 154(b) by 96 days.

(21) Appl. No.: 14/371,896

(22) PCT Filed: Mar. 15, 2013

(86) PCT No.: PCT/UA2013/000026
§ 371 (c)(1),
(2) Date: Jul. 11, 2014

(87) PCT Pub. No.: WO2013/141829
PCT Pub. Date: Sep. 26, 2013

(65) Prior Publication Data
US 2015/0246819 A1    Sep. 3, 2015

(30) Foreign Application Priority Data
Mar. 20, 2012  (UA) .................... 201203362

(51) Int. Cl.
*C01B 33/26*  (2006.01)
*C01F 17/00*  (2006.01)
(Continued)

(52) U.S. Cl.
CPC .............. *C01B 33/26* (2013.01); *A61K 33/00* (2013.01); *A61K 33/06* (2013.01); *B82Y 30/00* (2013.01);
(Continued)

(58) Field of Classification Search
None
See application file for complete search history.

(56) References Cited

U.S. PATENT DOCUMENTS 6,090,363 A * 7/2000 Green ................... B82Y 30/00
                                                  423/445 B
2005/0277367 A1* 12/2005 Fang ..................... C03C 19/00
                                                  451/41

(Continued)

OTHER PUBLICATIONS

Brichka et al., "Anticorrosion Properties of CeO2-Modified Aluminosilicate Nanotubes," Inorganic Materials, Jun. 2013, vol. 49, No. 6, pp. 581-585.*

(Continued)

*Primary Examiner* — David Sample
(74) *Attorney, Agent, or Firm* — Duane Morris LLP

(57) ABSTRACT

The application relates to cerium oxide-aluminosilicate tube nanocomposites. These nanocomposites can be used, for example, as components in pharmaceutical or cosmetic compositions. The nanocomposites of cerium oxide and aluminosilicate tubes contain 0.5-30% by weight of cerium oxide. The size of the cerium oxide nanoparticles is 4-15 nm. The cerium oxide-aluminosilicate tube nanocomposites are prepared by a method including the following steps: (i) preparation of an aqueous suspension of aluminosilicate tubes; (ii) deposition of cerium oxide by adding of solutions of cerium nitrate and ammonium hydroxide to stirred aqueous suspension of aluminosilicate tubes; (iii) filtering of formed sediment with subsequent washing of the sediment.

(Continued)

Figure 1:
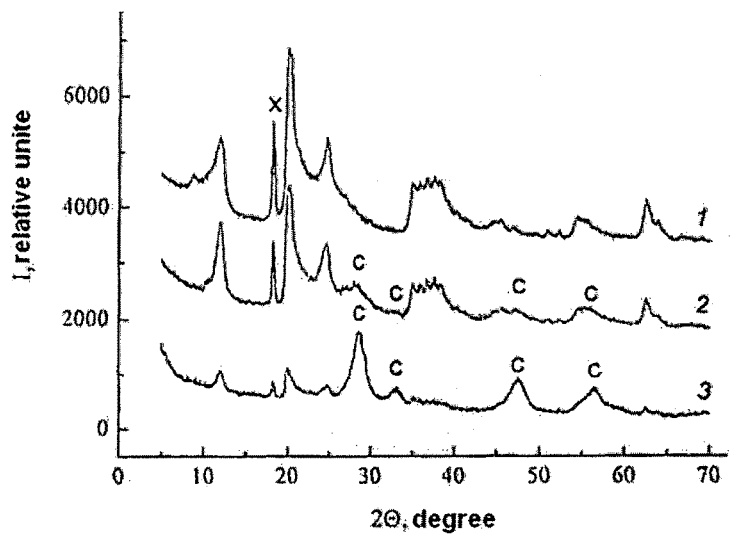

The addition of cerium nitrate and ammonium hydroxide solutions is carried out gradually.

3 Claims, 2 Drawing Sheets

(51) Int. Cl.
    *A61K 33/00*     (2006.01)
    *A61K 33/06*     (2006.01)
    *B82Y 30/00*     (2011.01)

(52) U.S. Cl.
    CPC ...... *C01F 17/0043* (2013.01); *C01P 2004/04* (2013.01); *C01P 2004/13* (2013.01); *C01P 2004/64* (2013.01); *C01P 2006/12* (2013.01); *Y10T 428/256* (2015.01)

(56) References Cited

U.S. PATENT DOCUMENTS

2007/0293714 A1* 12/2007 Long .................... B01J 29/405
    585/899
2012/0252845 A1* 10/2012 Engqvist .............. A61K 9/1611
    514/329
2015/0118422 A1* 4/2015 Busolo Pons .......... B01J 35/023
    428/35.3

OTHER PUBLICATIONS

Chen et al. "Facile synthesis of CeO2 nanotubes templated by modified attapulgite," Journal of Rare Earths, vol. 28, No. 4, Aug. 2010, p. 566-567.*

Gorobinskii et al., "Production of high porosity nanoparticles of cerium oxide in clay," Microporous and Mesoporous Materials 100 (2007) 134-138.*

Levis, "Characterisation of halloysite for use as a microtubular drug delivery system," International Journal of Pharmaceutics 243 (2002) 125-134.*

You et al., "Preparation, characterization and catalytic oxidation property of CeO2/Cu2+-attapulgite (ATP) nanocomposites," Journal of Rare Earths, vol. 28, Spec. Issue, Dec. 2010, p. 347-352.*

* cited by examiner

CERIUM OXIDE-ALUMINOSILICATE TUBES NANOCOMPOSITE AND METHOD OF PREPARATION

FIELD OF THE INVENTION

Chemical industry. Essence of the invention: cerium oxide aluminosilicate tubes nanocomposite. This nanocomposite can be used particularly in pharmaceutics or cosmetology (preparation of pharmaceutical or cosmetic composition component, e.g.).

Applicant knows the analogous methods of obtaining cerium oxide nanocomposite and cerium oxide nanocomposites obtained in these ways. The following methods are the most similar to the proposed method according to the group of dominant features.

The method of obtaining cerium dioxide nanoparticles in montmorillonite is known. Cerium dioxide can be precipitated by ammonium hydroxide in the presence of montmorillonite and the sediment (cerium dioxide deposited on montmorillonite) can be separated and washed [1]. Amorphous material with developed surface and increased porosity (micropore volume 0.1839 $cm^3 \cdot g^{-1}$, micropore diameter 3.07 nm) has been obtained in this way. Size of cerium dioxide particles has been estimated as 0.8-6.7 nm.

The following method of preparing of cerium oxide silicium oxide nanocomposite with highly developed specific surface also is technically close to the method proposed by declarant. This nanocomposite is prepared from a solution of cerium nitrate in chloric or nitric acid; sodium silicate should be contained in this solution. The reaction mixture is processed by ammonia vapour and acetone in autoclave at 500° C. Specific surface of end product was characterised as 140-200 $m^2 \cdot g^{-1}$, size of cerium dioxide particles was estimated as 2-6 nm [2].

The following method of obtaining of fine coatings of cerium oxide is known. Cerium oxide film is formed on a steel surface by means of the method of electrolyte deposition from cerium chloride-water-ethanol mixture. Three-electrode glass cell was used [3]. Such coatings can be used for steel corrosion protection. Sigma-Aldrich highest quality reagents were used. Cerium oxide was prepared by precipitation of cerium chloride from water solution after adding sodium hydroxide solution. The sediment was filtered and dried during 24 h in air at room temperature. An analogous process was performed for cerium chloride solution containing hydrogen peroxide ($H_2O_2$); hydrogen peroxide was used for complete oxidation of Ce(III) to Ce(IV).

The method of obtaining cerium oxide on the surface of particles of monodisperse silica is known. Peptised cerium oxide solution prepared, from cerium nitrate and sodium hydroxide in the presence of hydrogen peroxide was added to monodisperse silica [4]. Crystalline coating of cerium oxide was formed on silica surface at 60° C.; coating thickness can be varied by change of precursor solution concentration.

The method and equipment for preparation of crystalline cerium oxide nanoparticles with defined size limits are known [5]. One-time yield of cerium oxide reaches 70 g. Monodisperse nanoparticles of cerium oxide can be obtained from cerium nitrate-he xamethylenetetramine aqueous solutions; mixture was kept at 50° C. and the sediment formed was separated. In this case ammonium hydroxide is formed due to the interaction of water and ammonia generated in slow reaction of hexamethylenetetramine hydrolysis (formaldehyde is also formed in this process).

The new method of synthesis of cerium oxide nanoparticles with size from 2 to 10 nm and with increased bioactivity is also known [6]. These particles were used for investigation of increasing of cell vitality. Cerium oxide was obtained by means of the microemulsion method; water solution of cerium nitrate was added to toluene solution of sodium bis(ethylhexyl)sulfosuccinate (sodium docusate). This mixture was stirred during approx. 30 min., and 30% $H_2O_2$ was added to stirred solution. NaOH or $NH_4OH$ can be added in place of $H_2O_2$. Sodium docusate micelles act as "microreactors" for synthesis of cerium oxide nanoparticles. The solution was dried in nitrogen atmosphere; dry product was re-suspended in water before usage in biological experiments.

The method of preparation of cerium oxide with size from 5 to 50 nm and specific surface according to BET-method from 25 to 150 $M^2 \cdot g^{-1}$ is also known [7]. 2-ethylhexanoate and/or cerium laurate were atomised and oxidised by oxygen-containing gas. The cerium oxide particles obtained have carbonate groups on surface and in subsurface zone. The concentration of carbonate groups decreases on the surface. Carbon content in surface carbonate groups is from 5 to 50% of area and carbon content in carbonate groups at a distance of 5 nm from surface is 0-30% of area.

It is also known that nanoparticles of cerium oxide with additives of rare earth elements and transition metals can be obtained by means of (1) co-precipitation method, (2) burning of mixture of respective metal salts with glycine or aliphatic alcohols at 600-1000° C., (3) chemico-mechanical method with use of ball mill and respective metal hydroxides, carbonates, sulphates or oxychlorides and sodium chloride [8]. It was planned that obtained product will be used as catalyst for decreasing the toxicity of exhaust gases. Crushing of particles of product in organic solvent in the presence of organic acid, anhydride, ether or Lewis acid can be used for prevention of particle agglomeration.

It is known that nanocrystals of cerium oxide with various sizes and forms can be obtained through cerium-SAS (surface-active substance) complex [9]. Cerium-containing precursor interacts with SAS in organic medium following which, the thus formed cerium-SAS complex can be aged at 100-360° C. Such compounds as cerium acetate, acetylacetonate, fluoride, chloride, bromide, iodide, carbonate, nitrate, sulphates, oxalate, 2-ethylhexanoat, hydroxide etc. can be used for preparation of cerium oxide nanocrystals. Oleic, decanoic, octanoic, stearic acids, triphenylphosphine, trioctylphosphine, alkylamines etc. can be used as SAS.

The method of obtaining of cerium oxide powder with particle size from 50 nm to 3 μm and specific surface 20-250 $M^2 \cdot g^{-1}$ includes such stages as (1) cerium oxide precipitation from cerium nitrate, cerium acetate etc. by potassium hydroxide, sodium hydroxide or ammonium hydroxide, (2) cerium oxide oxidation by hydrogen or ammonium peroxide, ammonium persulfate $(NH_4)_2S_2O_8$, acids-oxidizers (perchloric acid $HClO_4$, permanganic acid $HMnO_4$, chromic acid H2CrO4 etc.) or oxygen-containing gases [10]. This powder is used as a polishing agent. Powder was separated, washed and dried during 24 h. Non-ionic dispersive polymers (polyvinyl alcohol, ethylene glycol, glycerol, polyethylene glycol, polypropylene glycol, polyvinylpyrrolidone) and anionic polymers (polyacrylic acid, ammonium polyacrylate, polyacrilmaleic acid) were used.

The method of preparation of cerium dioxide nanotubes from soluble cerium salts with the use of sodium hydroxide as precipitant is also known. The reaction was performed in base medium further reaction mixture was heated during 10-24 h. at 100-160° C. The sediment formed was separated, washed and dried at room temperature. The sediment was subjected to ultrasound during 1-2 h. in hydrogen peroxide medium. The cerium dioxide nanotubes were separated, washed and dried. The obtained cerium dioxide nanotubes have wall thicknesses from 5 to 7 nm and inner diameter of 10-20 nm [11].

The method of preparation of cerium dioxide polycrystals as nanobelts is known [12]. The three stages of this method are the following. Addition of $Ce(NO_3)_3 \cdot 6H_2O$ to stirred solution of PVP (polyvinylpyrrolidone) and dimethyl formamide $(CH_3)_2NC(O)H$; 2) obtaining of PVP-$Ce(NO_3)_3$ nanocomposite belts by electro-spinning, 3) obtaining of nanobelts from cerium dioxide polycrystals by heat treatment at 600-800° C. during 5-10 h with subsequent cooling. Nanobelts from cerium dioxide polycrystals (width 3-5 μm, thickness 65-120 nm, length 500 μm) were thus obtained.

The method of preparation of cerium dioxide spherical material is also known [13]. The stages of this method are as follows: (1) hydrothermal reaction between cerium nitrate and sodium citrate (molar reactant ratio 2:1-4:1; reaction is carried out in stirred solution (magnetic stirrer is used) during 4 24 h. at 120-200° C.). The product obtained was separated by centrifuging and washed with deionised water and ethanol. Product was dried during 8-10 h. at 60° C.; cerium dioxide spherical material was obtained. This material is characterised by a great number of active planes, stable spheroidal structure and improved catalytic properties.

The method of preparation of uniform-sized cerium dioxide nanopowders is also known; this material can be used as part of a polishing compound. Suspension of cerium oxide powder was introduced in comb-like co-polymer with the main chain formed from ionic polymers and side chains formed from non-ionic polymers. Average size of cerium oxide particles in this material is approx. 100 nm [14].

It is also known that cerium dioxide nanoparticles can be prepared by the method with the following stages: (1) interaction of water solution containing cerium ions, water solution containing hydroxide ions, water solution containing stabilizer of nanoparticles in presence of oxidizer; start temperature not exceeding 20° C.; (2) mechanical filtration of obtained mixture with following passing the mixture through perforated membrane; (3) formation of cerium hydroxide nanoparticles and (4) increase of temperature for oxidizing of cerium and obtaining of cerium dioxide. Cerium dioxide nanoparticles with average inner diameter 1-15 nm was thus obtained [15].

The method of preparation of clay intercalated by cerium dioxide nanoparticles by means of adding a purchasable colloidal solution of cerium oxide (Nyacol Products, Inc.; cerium oxide content 17%; particle size 5-10 nm) to the clay and prolonged (40 h.) stirring of the mixture was used as prototype [16]. Obtained material was separated by centrifuging and dried at 110° C. during 10 h.

The prototype method and analogous methods have a common defect: the usage of silica (analogous methods) or clay (prototype method) and certain special features of stirring and cerium oxide sedimentation complicate these methods and increase of the cost of the end products.

The main objective of performed work: obtaining of cerium oxide aluminosilicate tubes nanocomposite.

The problem was solved since cerium oxide aluminosilicate tubes nanocomposite was obtained; content of cerium oxide nanoparticles is 0.5-30%, size of cerium oxide nanoparticles is 4-15 nm.

The stages of the method of preparation of cerium oxide aluminosilicate tubes nanocomposite are as follows: (1) preparation of water suspension of aluminosilicate tubes; (2) deposition of cerium oxide by adding of solutions of cerium nitrate and ammonium hydroxide to stirred water suspension of aluminosilicate tubes; (3) filtering of formed sediment with following washing of the sediment; herewith the adding of cerium nitrate solution and ammonium hydroxide solution is carried out by degrees.

Additionally, the rate of adding of ammonium hydroxide solution to water suspension of aluminosilicate tubes is 0.02-0.05 ml·s$^{-1}$.

The following relationship of cause and effect exists between combination of critical limitations of invention and obtained technical result. Aluminosilicate tubes occur naturally; purchasable material obtained from halloysite mineral (Aldrich halloysite tubes) was used in this work. The chemical formula of halloysite is $Al_2Si_2O_5(OH)_4 \cdot nH_2O$, where n=0-2. The water molecules are placed between crystalline solid layers. Data of chemical composition, crystal and surface structures and spectral signature of HNT (halloysite nanotubes) are given in the review [17].

Aluminosilicate tubes were used for the first time for deposition of cerium dioxide.

Halloysite nanotubes are non-biodegradable and biocompatible that enables their use in medicine, veterinary medicine, cosmetology and agro-chemistry [18]. Modification of nanotubes leads to change of its functional properties.

Nanocrystalline cerium dioxide manifests unique antioxidant properties and has low toxicity [19].

According to the invention the sizes of cerium oxide crystals deposited on aluminosilicate tubes of obtained nanocomposite are 4-15 nm.

Also according to the invention the usage of aluminosilicate tubes instead of silica (according to analogous methods) or clay (according to prototype method), the increase of stirrer speed and the prolongation of the of ammonium hydroxide stage addition lead to formation of smaller particles of cerium oxide.

Diffractograms of aluminosilicate tubes (line 1), cerium oxide aluminosilicate tubes nanocomposite with 5% of cerium oxide (line 2) and cerium oxide aluminosilicate tubes nanocomposite with 30% of cerium oxide (line 3) are shown in FIG. 1, where c is $CeO_2$ phase and x is impurities in aluminosilicate tubes.

Figure 2:
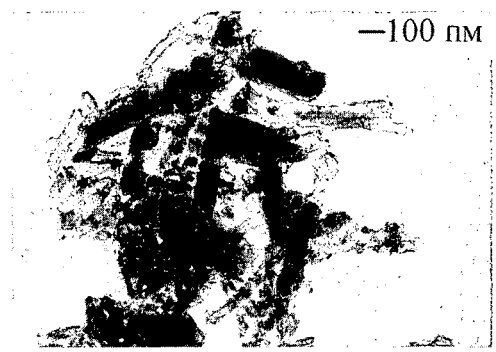
Figure 3:
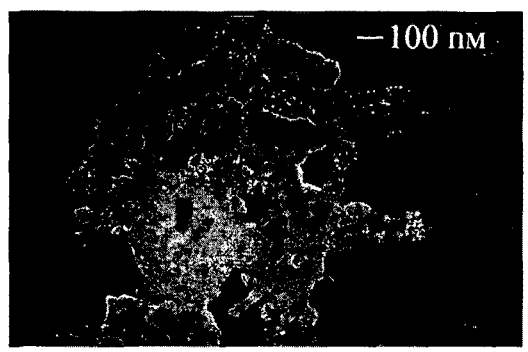
Figure 4:
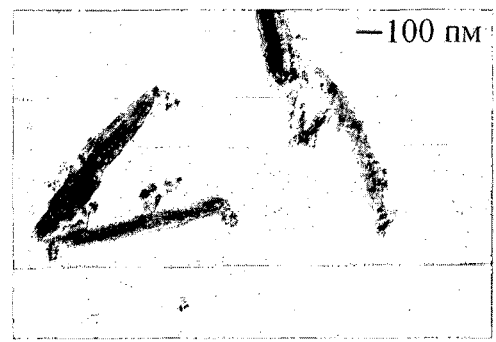
Figure 5:
Figure 6:
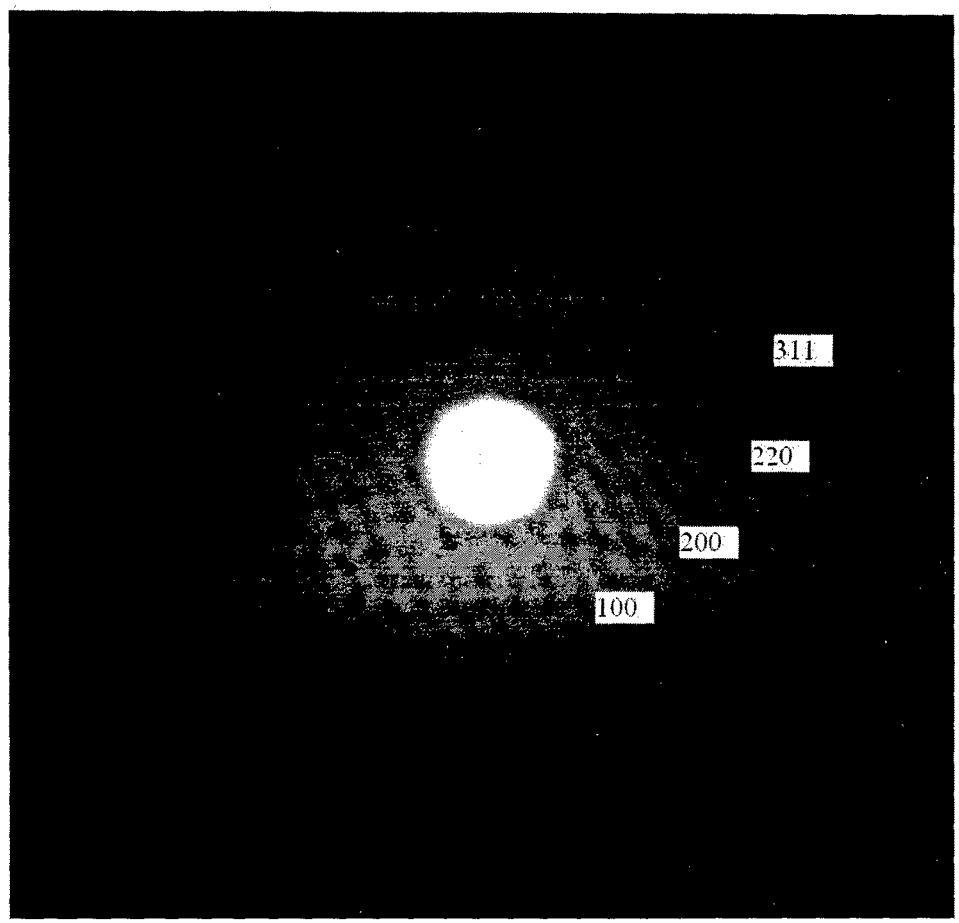

The results of electron-microscope investigation and electron diffraction analysis of cerium oxide aluminosilicate tubes nanocomposite are shown on FIG. 2-FIG. 6:

FIG. 2—transmission bright field electronic image of cerium oxide aluminosilicate tubes nanocomposite with 5% of cerium oxide, FIG. 3—transmission dark field electronic image of cerium oxide aluminosilicate tubes nanocomposite with 5% of cerium oxide, FIG. 4—transmission bright field electronic image of cerium oxide aluminosilicate tubes nanocomposite with 30% of cerium oxide, FIG. 5—transmission dark field electronic image of cerium oxide aluminosilicate tubes nanocomposite with 30% of cerium oxide, FIG. 6—electron diffraction pattern of $CeO_2$ particle on nanocomposite aluminosilicate tube.

These figures which illustrate the invention and present an example of the method of preparation of nanocomposite in no case limit the extent of claim according to the formula of invention, and only illustrate the essence of the invention.

The proposed method was implemented as follows.

300 g of aluminosilicate tubes were placed in 6 l reaction flask and 1200 ml of water was added. 183.48 ml of 0.5 M Ce(NO$_3$)$_3$ was added to the stirring mixture. 275.22 ml of 1 M NH$_4$OH was added to stirring suspension to pH 8-9 (base medium). The duration of NH$_4$OH addition was regulated by the opening of dropping funnel valve; hydrogen peroxide can be used. Approximate rate of addition of ammonium hydroxide solution was 0.02-0.05 ml·s$^{-1}$. Nanocomposite with 5% of cerium dioxide was thus obtained.

The suspension was mixed by mixing paddles driven by an electric motor. Rate of mixing exceeded 50 rpm. Rate of mixing corresponds to the rate of reagent adding.

The deposition process was carried out at room temperature. Sediment was filtered on Buchner funnel through layer of filter paper. Terminal residual pressure in Bunsen flask was 13-16 GPa; water pump was used. The sediment was washed by distilled water to negate nitrate quality reaction (reaction with diphenylamine in sulphuric acid) and dried in baker at 120° C. and 150° C. to constant weight. Conventional procedure of determination of moisture content in the sediment was used. Samples of CeO$_2$/aluminosilicate tubes composite with 0.5, 1, 2, 3, 4, 5, 20 and 30 m/m % of cerium oxide were obtained. These samples were investigated by electron microscope and selected area electron diffraction methods; such devices as Hitachi H-800, MIRA3 LMU, TESCAN were used. X-ray analysis (ДРОН-2М spectrograph with Cu Kα emission) was also used. Specific surface was estimated by Ar thermal desorption method after warming of the samples at 150° C.

According to obtained results the distribution of outer diameters of aluminosilicate tubes has maximum at 50 nm, and position of maximal distribution of inner diameters of aluminosilicate tubes (14 nm) suggest considerable wall thickness. Diffraction spectrum of hydrated halloysite has specific d$_{001}$ signal at 10.1 Å (halloysite-(10 Å)). The aluminosilicate dehydratation is an irreversible process, which leads to formation of halloysite-(7 Å) with limited low value of d$_{001}$=7.14 Å. The quantity of layers in aluminosilicate tubes is 18-25 for wall thickness of approx. 18 nm depending on dehydratation degree. The length of these tubes varies from tens to hundred nanometers; prevailing values are from 100 to 600 nm.

According to the results of electron-microscope investigation, the materials obtained contain not only tubes but also sections without tube morphology and cavities. Results of electron diffraction investigation of particles with d(hkl)=3.12 (100), 2.7 (200), 1.89 (220) and 1.64 A (311) signals suggest that these particles are in the cubic phase of cerium dioxide. Signal in the area of 2Θ=18° on diffractograms can be connected with the presence of halloysite impurity (probably allophanite). Small angle signals on diffractograms correspond to presence of tubular halloysite-(7 Å) and -(10 Å). 10 Å signal disappears after modification of aluminosilicate tubes by cerium dioxide and it can be connected with desorption of halloysite interlayer water. Essential signal half-width can be explained by small sizes of cerium dioxide crystals.

The sizes of cerium dioxide particles are 4-11 nm for CeO$_2$/aluminosilicate tubes nanocomposite with 5% CeO$_2$ and 6-15 nm for CeO$_2$/aluminosilicate tubes nanocomposite with 30% CeO$_2$. It is obvious that the increase of cerium nitrate concentration leads to the formation of bigger particles. The conclusion can be made that the properties of aluminosilicate tubes influence the sizes of cerium dioxide nanoparticles.

It must be noted that the proposed method can be used for the preparation of cerium oxide aluminosilicate tubes nanocomposite with/without addition of hydrogen peroxide. In particular, the reaction formula without hydrogen peroxide is as follows:

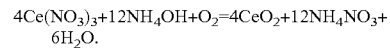

Reaction formula with usage of hydrogen peroxide (hydrogen peroxide solution should be added to stirred reaction mixture after ammonium hydroxide) is as follows:

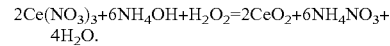

Both procedures lead to the formation of CeO$_2$/aluminosilicate tubes nanocomposite with identical morphology and chemical composition.

It should be noted that the proposed method of nontemplate synthesis decreases the cost of obtaining nanosized. CeO$_2$. The sizes of particles can be decreased if such costs as usage of special templating additives, ultrasound treatment etc. will be used.

BIBLIOGRAPHY

1. Gorobinskii L. V., Yurkov G. Yu., Baranov D. A. Production of high porosity nanoparticles of cerium oxide in clay//Microporous and Mesoporous Materials.-2007. -100. -P. 134-138.
2. Lopez I., Valdes-Solis T., Marban G. The synthesis of high surface area cerium oxide and cerium oxide/silica nanocomposites by the silica aquagel-confined co-precipitation technique//Microporous and Mesoporous Materials.-2010. -127. -P. 198-204.
3. Creus J., Brezault F., Rebere C., Gadouleau M. Synthesis and characterisation of thin cerium oxide coatings elaborated by cathodic electrolytic deposition on steel substrate//Surface & Coatings Technology.-2006. -200. -P. 4636-4645.
4. Oh M. -H., Lee J. -S., Gupta S., Chang F. -Ch., Singh R. K. Preparation of monodispersed silica particles coated with ceria and control of coating thickness using sol-type precursor//Colloids and Surfaces A: Physicochem. Eng. Aspects.-2010. -355. -P. 1-6.
5. U.S. Pat. No. 7,141,227, publication date 28 Nov. 2006, IPC (International Patent Classification): C 01F 1/00, C 01F 17/00, B 01F 7/00.
6. U.S. Pat. No. 7,534,453, publication date 19 May 2009, IPC: A 01N 59/16, A 61K 33/24.
7. U.S. Pat. No. 7,553,465, publication date 30 Jun. 2009, IPC: B 23B 19/00, B 32B15/02, B 24B 1/00, C 01F 1/00.
8. US20050066571, publication date 31 May 2005, IPC: C 01L 1/12.
9. US20070092423, publication date 26 Apr. 2007, IPC: C 01F 17/00.
10. US20100044625, publication date 25 Feb. 2010, IPC: C 01F 17/00, B 23B 5/16.
11. CN 101205078, publication date 09 Jun. 2010, IPC: C01F17/00.
12. CN 101792170, publication date 04 Aug. 2010, IPC: B82B3/00; CO1F17/00.
13. CN 101857260, publication date 13 Oct. 2010, IPC: B82B3/00; C01F17/00.
14. KR 20110090631, publication date 10 Aug. 2011, IPC: B82B3/00; C01F17/00.
15. US 20110056123, publication date 10 Mar. 2011, IPC: B82Y40/00; C01L1/188, C01F17/00, C10L1/12, C09K3/14.
16. U.S. Pat. No. 4,637,992, publication date 20 Jan. 1987, IPC: B01.121/16.

17. Brichka S. Ya. Natural aluminosilicate nanotubes: structure and properties//Nanostrukturnoe materialovedenie.-2009. -2. -P. 40-53. Бричка С.Я. Природные алюмосиликатные нанотрубки: структура и свойства // Наноструктурное материаловедение. -2009. -2. -С. 40-53.)

18. Levis S. R., Deasy P. B. Characterisation of halloysite for use as a microtubular drug delivery system//International Journal of Pharmaceutics.-2002. -243. - P. 125-134.

19. Ivanov V. K., Scherbakov A. B., Usatenko A. B. Structure-sensitive properties and biomedical applications of nanodisperse cerium dioxide//Uspechi chimii.-2009. -78, 9. -P. 924-941. (Иванов В.К., Щербаков А.Б., Усатенко А.В. Структурно-чувствительные свойства и применения нанодисперсного диоксида церия//Успехи химии.-2009. -78, 9. -С. 924-941.)

The invention claimed is:

1. A method of preparation of a cerium oxide halloysite tubes nanocomposite comprising: (i) preparation of a water suspension of halloysite tubes; (ii) deposition of cerium oxide at room temperature by addition of solutions of cerium nitrate and ammonium hydroxide to a stirred water suspension of halloysite tubes; and (iii) filtering of formed sediment with subsequent washing of the sediment; wherein the adding of cerium nitrate solution and ammonium hydroxide solution is carried out by degrees.

2. The method according to claim 1, characterized in that the rate of adding of ammonium hydroxide solution to the water suspension of halloysite tubes is between 0.02 ml per second and 0.05 ml per second.

3. The method according to claim 1, characterized in that addition of 0.5 M cerium nitrate solution and 1 M ammonium hydroxide solution is performed.

* * * * *